United States Patent [19]

Rivadeneyra

[11] Patent Number: 4,469,096

[45] Date of Patent: Sep. 4, 1984

[54] SUPPLEMENTAL HAND RESTRAINT DEVICE

[75] Inventor: Ricky R. Rivadeneyra, San Clemente, Calif.

[73] Assignee: Soft Cell Products, San Clemente, Calif.

[21] Appl. No.: 410,716

[22] Filed: Aug. 23, 1982

[51] Int. Cl.³ .............................................. A61F 13/00
[52] U.S. Cl. ................................................... 128/133
[58] Field of Search .............. 128/133, 134, 161, 162, 128/165, 157

[56] References Cited

U.S. PATENT DOCUMENTS

| | | | |
|---|---|---|---|
| 1,048,098 | 12/1912 | Rheubottom | 128/134 |
| 2,030,091 | 2/1936 | Behringer | 128/134 |
| 2,416,800 | 3/1947 | Moller | 128/133 |
| 2,645,922 | 7/1953 | Martin | 128/133 |
| 2,828,738 | 4/1958 | Strelakos | 128/134 |
| 2,949,761 | 8/1960 | Mitchell et al. | 128/133 |
| 3,007,331 | 11/1961 | Irwin | 128/133 |
| 3,361,132 | 1/1968 | Reutsch | 128/134 |
| 3,476,108 | 11/1969 | Matukas | 128/133 |
| 4,024,863 | 5/1977 | Ball | 128/133 |
| 4,173,974 | 11/1979 | Bellireau | 128/133 |

FOREIGN PATENT DOCUMENTS 18133 of 1912 United Kingdom ................ 128/133

Primary Examiner—C. Fred Rosenbaum
Assistant Examiner—C. W. Shedd
Attorney, Agent, or Firm—Hubbard & Stetina

[57] ABSTRACT

A supplemental hand restraint device is disclosed which is utilized in conjunction with conventional handcuffs to eliminate functional hand and/or finger use of a person in custody. The device comprises a bag adapted to be positioned over the hands and handcuffs of a person in custody and be secured thereupon to completely enclose or encapsulate the person's hands. The device may additionally be secured to the belt of a person in custody to prevent the person from stepping through the handcuffs as well as be utilized in multiple custody applications.

9 Claims, 6 Drawing Figures

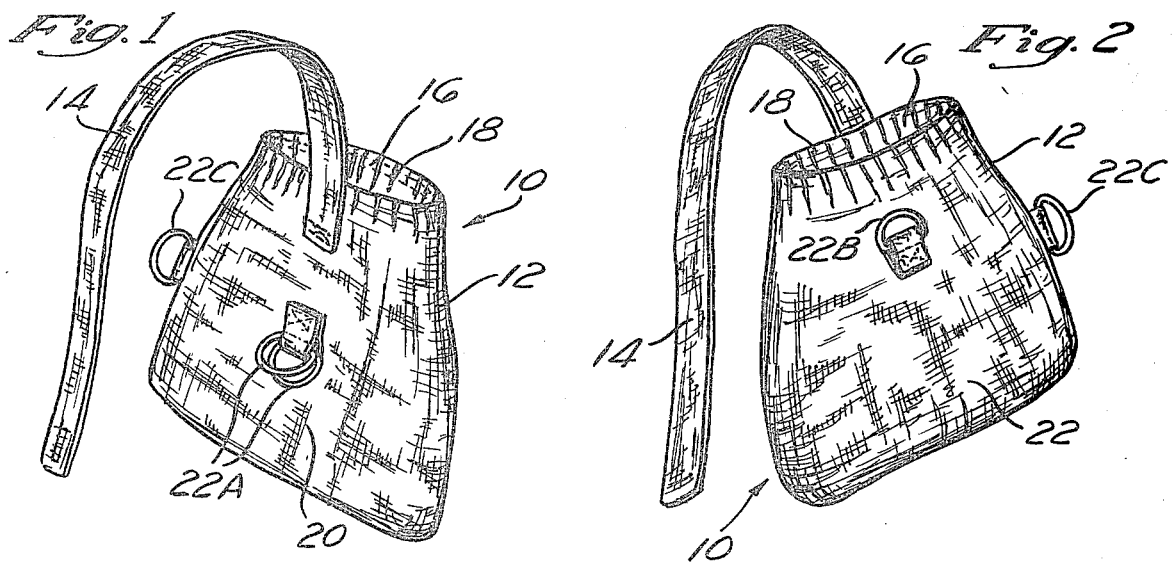
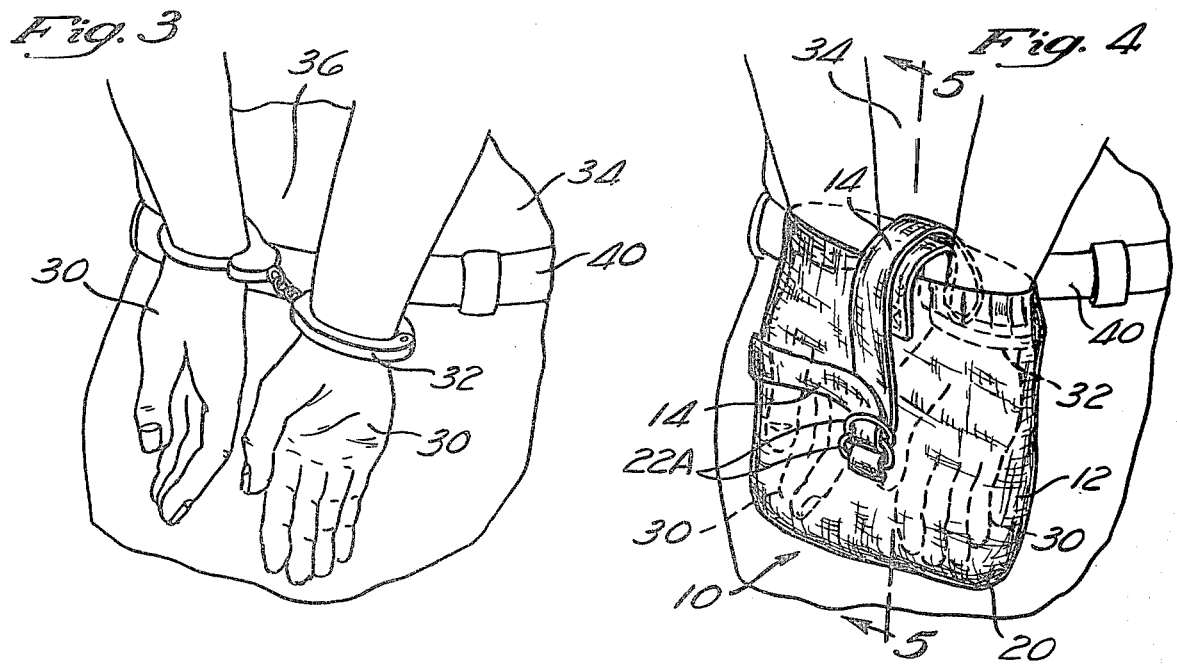
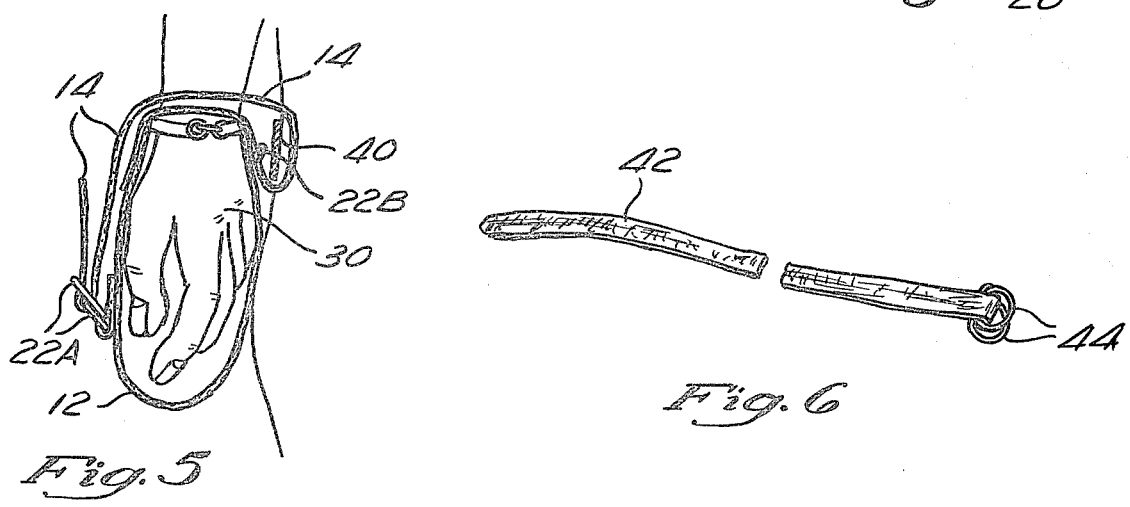

SUPPLEMENTAL HAND RESTRAINT DEVICE

BACKGROUND OF THE PRESENT INVENTION

The present invention relates to hand restraints and, more particularly, to a supplemental hand restraint device which is utilized in conjunction with conventional handcuffs to eliminate functional hand or finger use of a person in custody.

As is well known, it is conventional practice for law enforcement and security officers to utilize handcuffs in an attempt to physically control a person in custody. Such handcuffs are typically applied tightly about the wrists of the person in custody to secure the person's hands together either in front of or behind the back. Although such prior art handcuffs have proven to be useful in general applications, they possess inherent deficiencies which have detracted from their overall effectiveness in the field.

Foremost of these deficiencies has been the inability of prior art handcuffs to render a suspect incapable of physical action. In this regard, law enforcement experience has shown that the physical control handcuffs provide over a person in custody is severely limited unless the person is constantly maintained under surveillance. Such limited control is manifested mainly due to handcuffs allowing a limited yet functional use of the person's hands and fingers which in many instances has allowed persons to destroy or jettison evidence after being placed in custody or in extreme instances, has permitted the in-custody person access to weapons resulting in countless injuries and numerous deaths to law enforcement officers.

In addition, the prior art handcuffs have often created a false sense of security for the law enforcement officer that has heretofore allowed in-custody persons to slide out of the handcuffs or alternatively step through the handcuffs and, thus, pose a significant safety hazard to the officer.

As such, there exists a substantial need in the art for an improved hand restraint device which is relatively low cost, may be easily carried and manipulated by an officer, and serves to eliminate the limited yet functional hand and finger use of a person in custody.

SUMMARY OF THE PRESENT INVENTION

The present invention specifically addresses and alleviates the above-referenced need associated in the art by providing a reliable physical control of in-custody persons while further ensuring officer safety and the preservation of evidence. More particularly, the present invention comprises a supplemental hand restraint device which is utilized in conjunction with conventional prior art handcuffs to eliminate the functional hand and finger use of in-custody persons.

In the preferred embodiment, the supplemental hand restraint device of the present invention is formed as a fabric bag, open at one end and sized to be positioned over the hands and handcuffs of an in-custody person. Once positioned over the hands, the fabric bag may be secured thereupon as by way of a closure strap which extends tightly over the open end of the bag and about the handcuffs. As such, the supplemental hand restraint device of the present invention completely encloses or encapsulates the person's hands, thereby substantially eliminating any finger and hand dexterity or manipulation which heretofore has permitted access to evidence, contraband, or weapons.

In addition, the present invention is adapted to permit the hands of an in-custody person to be securely restrained adjacent the person's waist thereby eliminating any possibility of the person stepping through the handcuffs while in custody. More particularly, during installation of the device upon the in-custody person, the securing strap may be laced around the belt of the person and subsequently pulled tightly thereabout to securely maintain the in-custody person's hands adjacent his belt.

Further, the present invention is specifically adapted to permit rapid attachment to plural supplemental hand restraint devices to accommodate multiple custody situations.

In addition, the supplemental hand restraint device of the present invention allows an officer to conduct safer and more efficient searches of an in-custody person, protects the officer from being grabbed or scratched by fingernails, and makes it impossible for the in-custody person to manipulate his cuffed hands from the rear of the body to the front of the body.

DESCRIPTION OF THE DRAWINGS

These as well as other features of the present invention will become more apparent upon reference to the drawings, wherein:

FIG. 1 is a front perspective view of the supplemental hand restraint device of the present invention;

FIG. 2 is a rear perspective view of the supplemental hand restraint device of the present invention;

FIG. 3 is a perspective view of an in-custody person depicting the conventional manner in which handcuffs are attached about the wrist of the person;

FIG. 4 is a perspective view of an in-custody person having the supplemental hand restraint device of the present invention installed about the hands and handcuffs of the in-custody person;

FIG. 5 is a cross-sectional view taken about lines 5—5 of FIG. 4; and

FIG. 6 is a perspective view of an auxiliary strap to be utilized in combination with the supplemental hand restraint device of the present invention.

DETAILED DESCRIPTION OF THE PREFERRED EMBODIMENT

Referring particularly to FIGS. 1 and 2, there is shown the supplemental hand restraint device 10 of the present invention composed generally of a bag portion 12 and strap portion 14. The bag portion 12 is formed having a closed bottom and closed sides and includes an open upper end 16. The uppermost edge of the open end 16 is preferably gathered and provided with an elastic liner 18 (represented by the phantom lines in FIGS. 1 and 2) which biasingly maintains the open end 16 in a reduced perimeter size. In the preferred embodiment, the overall dimensions of the bag portion 12 and opening 16 are sized to receive and extend over the hands and handcuffs 30 and 32, respectively, of an in-custody person 34 (shown in FIGS. 3 and 4) but typically is formed having a width of approximately 9 inches, a heighth of approximately 9 inches, and a minimum perimetric size of 12 inches along the opening 16.

The strap portion 14 comprises an elongate member which is rigidly attached at one end thereof to the front surface 20 of the bag portion 12 adjacent the opening 16. In the preferred embodiment, the strap portion 14 has an approximate width of 1 inch and a length of 16 inches and is formed of a tight weave nylon material. A pair of D-ring fasteners 22A is additionally secured to the front surface 20 of the bag portion 12 approximately midway along the heighth of the bag portion 12. Each of the D-rings 22A is sized to receive the width of the strap portion 14 and as will be explained in more detail infra, serve to secure the supplemental hand restraint device 10 upon the in-custody person 34. The rear surface 22 of the bag portion 12 is additionally provided with a single D-ring fastener 22B which is similarly sized to the pair of D-rings 22A and is rigidly attached to the bag portion 12 adjacent the opening 16. An auxiliary D-ring 22C is further secured to one side of the bag portion 12.

With the structure defined, the installation and operation of the supplemental hand restraint device 10 of the present invention may be described. Referring to FIG. 3, an in-custody person 34 is depicted and as in conventional practice, a pair of handcuffs 32 is positioned tightly about the person's wrists to maintain the hands 30 of the person 34 together. Preferably, the hands 30 are cuffed behind the back 36 of the person 34; however, the hands 30 may additionally be cuffed in front of the person 34 if desired.

With the hands 30 cuffed, the supplemental hand restraint device of the present invention may be installed upon the person 34 merely by manually stretching the elastic liner 18 positioned about the opening 16 and inserting the hands 30 of the person 34 into the interior of the bag portion 12. The hands 30 are inserted downward into the bag portion 12 of the device 10 through a sufficient distance such that the elastic liner 18 and opening 16 of the bag portion 12 is disposed slightly above the handcuffs 32, i.e. such that the handcuffs 32 and hands 30 are completely enclosed or encapsulated within the interior of the bag portion 12 (as depicted in FIG. 4). As will be recognized, with the device 10 positioned in such a manner, the releasing of the elastic liner 18 causes the opening 16 of the bag portion 12 to be reduced in size and therefore preliminarily retain the device 10 upon the person 34.

Subsequently, the strap portion 14 is extended from the front surface 20 of the bag portion 12 over the opening 16 and threaded through the D-ring 22B secured to the back surface 22 of the bag portion 12. Once threaded through the D-ring 22B, the strap member 14 is looped over, i.e. extended back over the opening 16 and pulled tightly or cinched to tightly close the opening 16 of the bag portion 12 above the handcuffs. The strap portion 14 may then be inserted through the pair of D-rings 22A secured to the front surface 20 of the bag portion 12 and subsequently inverted to loop over one of the pair of D-rings 22A as depicted in FIG. 4. As will be recognized, by such a procedure, the strap member 14 will be locked or retained in position by the pair of D-rings 22A. The distal end of the strap member 14 may subsequently be inserted through the auxiliary D-ring 22C so as not to dangle and be maintained adjacent the bag portion 12 and not dangle.

Due to the strap portion 14 extending over the opening 16 and above the handcuffs 30, it will be recognized that once installed, the supplemental hand restraint device 10 cannot be pulled off the hands 30 of the in-custody person 34. In addition, due to the hands 30 being maintained within the bag portion 12 of the device 10, finger dexterity and manipulation of the hands of the in-custody person 34 is substantially eliminated with the bag portion 12 preventing direct access of the hands 30 to weapons, evidence, contraband, or the like.

To completely secure the pair of hands 30 in a desired position and eliminate the person 34 from stepping through the handcuffs 32, the present invention 10 additionally contemplates the strap portion 14 to be looped about the belt 40 of the in-custody person 34. The particular manner in which this is accomplished is depicted in FIG. 5 and comprises insertion of the strap portion 14 behind the belt 40 subsequent to threading of the strap portion 14 through the D-ring 22B located on the back surface of the bag portion 12 and prior to extending the same back over the opening 16 toward the front surface 20 of the bag portion 12. As such, it will be recognized that due to the strap portion 14 looping over the belt 40, the hands 30 of the in-custody person 34 are securely anchored adjacent the waist of the person 34.

In those instances where the in-custody person is not wearing a belt 40, a supplemental strap portion 42 (depicted in FIG. 6) is provided and may be rapidly secured about the waist of the person 34 as by way of a pair of D-rings 44 located on the belt 42. Once secured about the person 34, the strap portion 14 of the device 10 may be looped about the supplemental strap 42 in the manner previously described. In addition, the supplemental strap portion 42 may be utilized in conjunction with the auxiliary D-ring 22C located on the side of the bag portion 12 to permit two or more supplemental hand restraint devices to be secured together for multiple custody applications.

Thus, in summary, it will be recognized that the supplemental hand restraint device 10 of the present invention comprises a relatively low cost and readily portable means for eliminating the functional hand and finger use of in-custody persons. Although in the preferred embodiment particular sizes and materials have been defined, those skilled in the art will recognize that modifications to the same can be made without departing from the spirit of the present invention and such modifications are clearly contemplated herein. In addition, although in the preferred embodiment the supplemental hand restraint device 10 of the present invention has been described for use upon the hands of an in-custody person, the device is further applicable for feet applications and for purposes of this application, the term "hand" shall be defined to include both hands and feet.

What is claimed is:

1. A supplemental hand restraint device comprising:
    a bag adapted to receive the hands and handcuffs of an in-custody person therein;
    an opening formed on end of said bag sized to permit said bag to be extended over the hands and handcuffs of said in-custody person to a position enclosing the hands and handcuffs of said person within said bag; and
    means for securing said bag in said position upon said in-custody person.

2. The device of claim 1 wherein said securing means comprises a strap attached to one side of said bag and adapted to extend over said opening and engage the other side of said bag to close said opening.

3. The device of claim 2 wherein said securing means further comprises means for maintaining said strap extended over said opening.

4. The device of claim 3 wherein said opening includes an elastic member formed to gather said bag together adjacent said opening.

5. The device of claim 4 wherein said bag is formed of a fabric material.

6. The device of claim 4 wherein said bag is formed of a canvas material.

7. A method of safely restraining the hands of a person comprising the steps of:

applying a pair of handcuffs to the wrists of a person to maintain the hands of said person proximal one another;

extending a bag over said hands and said pair of handcuffs to enclose said hands and said pair of handcuffs within the interior of said bag; and securing said bag about said hands and said pair of handcuffs.

8. The method of claim 7 wherein said bag includes an open end and said securing step comprises extending a strap over said open end of said bag to engage opposite sides of said bag and close said open end of said bag.

9. The method of claim 8 wherein said securing step further comprises the step of encircling said strap about a belt worn by said person to maintain the hands of said person adjacent the waist of said person.

* * * * *